United States Patent [19]

Finizio

[11] 4,065,453

[45] Dec. 27, 1977

[54] LEVOROTATORY MOLINDONE AND THE USE AS AN ANTIDEPRESSANT

[75] Inventor: Michael Finizio, Howard Beach, N.Y.

[73] Assignee: Endo Laboratories, Inc., Garden City, N.Y.

[21] Appl. No.: 737,658

[22] Filed: Nov. 1, 1976

[51] Int. Cl.$^2$ .................... A61K 27/00; C07D 295/00
[52] U.S. Cl. .............................. 424/248.56; 544/144
[58] Field of Search ............... 424/248.56; 260/247.5, 260/247.2 R

[56] References Cited

U.S. PATENT DOCUMENTS 3,491,093  1/1970  Pochter et al. ............... 260/247.2 R

*Primary Examiner*—Stanley J. Friedman

[57] ABSTRACT

The levorotatory enantiomer of molindone [3-ethyl-6,7-dihydro-2-methyl-5-(morpholinomethyl)-indol-4(5H)-one] has been isolated and found to have significantly greater antidepressant activity than the corresponding racemate.

3 Claims, No Drawings

LEVOROTATORY MOLINDONE AND THE USE AS AN ANTIDEPRESSANT

BACKGROUND OF THE INVENTION

U.S. Pat. No. 3,491,093, issued Jan. 20, 1970 to Irwin J. Pachter and Karl Schoen, discloses and claims the compound 3-ethyl-6 7-dihydro-2-methyl-5-(morpholinomethyl)-indol-4(5H)-one (molindone):

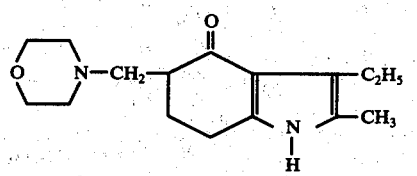

and salts thereof, the their use as antipsychotics. In particular, the Pachter patent discloses that molindone exhibits neuroleptic and antidepressant properties. Molindone hydrochloride is available commercially under the trademark Moban ® from Endo Laboratories, Inc., Garden City, N.Y.

SUMMARY OF THE INVENTION

The levorotatory enantiomer has now been isolated and has been found to have significantly greater antidepressant activity with approximately the same sedative and tranquilizer activity as the racemate. This unexpected combination of properties renders the levorotatory enantiomer of molindone more suited for pharmacological use as an antidepressant in agitated or retarded depressives. Accordingly, the present invention relates to the levorotatory enantiomer of molindone, pharmaceutical compositions containing the levorotatory enantiomer of molindone in the absence of any substantial amount of the dextrorotatory enantiomer, and methods of using such compositions as antidepressant agents, in particular in agitated or retarded depressives.

DETAILED DESCRIPTION OF THE INVENTION

Molindone can be made by the process disclosed at column 1, line 71 through column 3, line 2 of the above-mentioned U.S. Pat. No. 3,491,093 and column 2, line 62 through column 4, line 21 of the U.S. Pat. No. 3,636,042, issued to Irwin J. Pachter and Karl Schoen on January 18, 1972, which disclosures are hereby specifically incorporated by reference.

The levorotatory enantiomer of molindone can be isolated by repeated recrystallizations of the (+)-mandelic acid salt of molindone from acetone.

The preparation of molindone is illustrated by the following example. All parts, proportions and percentages are by weight unless otherwise indicated.

EXAMPLE 1

3-ethyl-6,7-dihydro-2-methyl-5-(morpholinomethyl)indol-4(5H)-one

3-Ethyl-6,7-dihydro-2-methylindol-4(5H)-one 14.1 gm. (0.08 mole), 14.8 gm. morpholine hydrochloride (0.12 mole), and 3.6 gm. paraformaldehyde (0.12 mole) were refluxed in 200 ml. ethanol for 40 hours. The solution was evaporated to dryness in vacuo on a steam bath and the residue digested with a mixture of 150 ml. water and 10 ml. 2 N HCl. An insoluble residue of unreacted starting material was filtered off. To the acid solution, ammonia water was added dropwise with stirring and the amine crystallized out. It was purified by dissolving in 1 N HCl and addition of ammonia, then by 2 crystallizations from benzene followed by 2 crystallizations from isopropanol to yield 3-ethyl-6,7-dihydro-2-methyl-5(morpholinomethyl) indol-4(5H)-one, (±)-molindone, m.p. 180°–181° C.

The isolation of the levorotatory enantiomer is illustrated by the following example.

EXAMPLE 2

23.6 Grams of molindone (m.p. 179°–180° C), such as prepared by the process of Example 1, above, and 13.0 grams of (+)-mandelic acid was dissolved in 175 ml. of hot acetone. This solution was cooled to 11° C; the resulting head fraction (HF 1) yielded 14.4 grams ($[\alpha]_D^{28} + 13.8°$ (c 1.05, MeOH)); the mother liquor (ML 1) was discarded. The head fraction (HF 1) was dissolved in 50 ml of boiling acetone, and the solution was cooled to 11° C; the resulting head fraction (HF 2) yielded 8.7 grams ($[\alpha]_D^{28} + 8.4°$ (c 1.02, MeOH)); the mother liquor (ML 2) was discarded. The head fraction (HF 2) was dissolved in 50 ml of boiling acetone, and the solution was cooled to 25° C; the resulting head fraction (HF 3) 1.1 grams ($[\alpha]_D^{28} + 3.3°$ (c 1.06, MeOH)) and was discarded. The mother liquor (ML 3) was cooled further to 11° C; the resulting head fraction (HF 3A) yielded 4.75 grams ($[\alpha]_D^{28} + 1.8°$ (c 1.04, MeOH)); the mother liquor (ML 3A) was discarded. The head fraction (HF 3A) was dissolved in 50 ml of boiling acetone, and the solution was cooled to 11° C; the resulting head fraction (HF 4) yielded 1.9 grams ($[\alpha]_D^{28} - 5.6°$ (c 1.06, MeOH)); the mother liquor (ML 4) was discarded. The head fraction (HF 4) was dissolved in 25 ml of boiling acetone, and the solution was cooled to 11° C; the head fraction (HF 5) yielded 0.4 grams ($[\alpha]_D^{28} - 12.7°$ (c 1.06, MeOH)); the mother liquor (ML 5) was discarded. The head fraction (HF 5) was dissolved in water, treated with excess 1N sodium hydroxide. The product was extracted into chloroform, and the chloroform extracts were washed with water and dried over potassium carbonate. Evaporation gave a solid which was crystallized from a mixture of benzene and ethanol, giving 200 mg. of needles, (−)-molindone, m.p. 151.5°–152° C. ($[\alpha]_D^{27} - 138°$ (c 1.027, 1 N HCl)).

The compound of the present invention displays central nervous system activity, and in particular, shows useful psychotherapeutic activity as an antidepressant agent, especially useful for agitated depressives.

The activity of this compound has been demonstrated in the following laboratory tests:

(1) Tetrabenazine Antagonism (Anti-TBZ)

Groups of 10 Carworth $CF_1S$ female mice, 18–21 g each, were fasted 1.5 hours and were incubated with antagonist compounds at oral doses of 0, 5, 25, and 125 mg/kg or 0, 1, 3, 9, 27, and 81 mg/kg in 0.20 ml of 1% Methocel. The mice were challenged 30 minutes later with tetrabenazine (as the methanesulfonate), 32 mg/kg intraperitoneally (dissolved in 0.20 ml 0.05M KCl at pH 2.0). One hour after antagonist (30 minutes after tetrabenzaine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5 × 8 inches with 0.33 inch mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes. The results from this test, in mg/kg. p.o., are given in Table 1.

(2) Exploratory Loss

The mouse is placed on a stainless steel wire mesh screen (8 × 12 inches, 3 mesh per inch, ¼inch mesh openings) "shoe-box" lid (1inch high) and is observed for normal activities, such as nose movements, head movements with apparent visual examination of the area, and/or walking around on the screen. Normal mice respond within 2 to 3 seconds. Absence of or a marked depression of these activities for 5 seconds constitutes a loss of exploratory activity.

The results from this test, in mg/kg p.o., are given in Table 1.

(3) Rat Conditioned Avoidance Response (rat CAR)

Blocking of CAR in rats at nontoxic doses correlates with major tranquilizer activity in man.

Rats are trained to jump out of a pit onto a ledge to avoid shock when presented with a conditioned stimulus of light and sound. Three or four doses of durg are given to a group of 4–8 rats. The animals are tested 1, 2 and 4 hours after dosing. A quantal $ED_{50}$ is calculated as the dose which would block the CAR in 50% of the rats. The results are given in mg/kg., p.o. (Table 1)

The $ED_{50}$'s for the compound of the present invention and for the molindone racemic mixture are given in the following table, along with certain appropriate ratios:

Table 1

| | $ED_{50}$ values | | | ratios | |
| | mouse | | rat | | |
| | ANTI-TBZ | EXPL. | | | |
| | ptosis | expl. loss | LOSS | CAR | col. 3/col. 1 | col. 4/col. 1 |
|---|---|---|---|---|---|---|
| (−)-molindone* | 2.7 | 3.4 | 25.0 | 21.0 | 9.3 | 7.8 |
| (±)-molindone | 7.2 | 9.0 | 38.0 | 28.0 | 5.3 | 3.9 |
| ratio: $\frac{(\pm)\text{-molindone}}{(-)\text{-molindone}}$ | 2.7 | 2.6 | 1.5 | 1.3 | — | — |
| column no. | 1 | 2 | 3 | 4 | 5 | 6 |

*levorotatory enantiomer of molindone

As can be seen from the above data, the levorotatory enantiometer is unexpectedly 2.7 times as potent as the racemate as an antidepressant, but only 1.5 times as potent as a sedative and 1.3 times as potent as an antipsychotic.

The ratios in the table demonstrate the clear separation of the antidepressant activity from the sedative activity for the levorotatory enantiomer as compared with the racemate. Such a separation is not only quite useful, but is also quite surprising and unexpected.

The compound of the present invention can be administered orally or parenterally. A useful oral dose would be at a level of about 0.02–100 mg/kg, preferably 0.1–25 mg/kg, and most preferably about 0.5–5 mg/kg of body weight. The useful human dose is expected to be in the range of about 50–150 mg/day.

The compound of the present invention can be formulated into compositions comprising the compound together with a pharmaceutically suitable carrier. The carrier can be either a solid or liquid and the compositions can be in the form of tablets, liquid-filled capsules, dry-filled capsules, aqueous solutions, non-aqueous solutions, injectables, suppositories, syrups, suspensions and the like. The compositions can contain suitable preservatives and coloring and flavoring agents. Some examples of the carriers which can be used in the preparation of the products of this invention are gelatin capsules; sugars, such as lactose and sucrose; starches; dextrans; cellulosics, such as methyl cellulose, cellulose acetate phthalate; gelatin; talc; steric acid salts; vegetable oils, such as peanut oil, cottonseed oil, sesame oil, olive oil, corn oil, and oil of theobroma; liquid petrolateum; polyethylene glycol; glycerin, sorbitol; propylene glycol; ethanol; sodium metabisulfite, disodium ethylenediaminetetraacetic acid; agar; water; and isotonic saline.

In formulating the compounds, conventional practices and precautions are used. The composition intended for parenteral administration must be sterile either by using sterile ingredients and carrying out the production under aseptic conditions or by sterilizing the final composition by one of the usual procedures such as autoclaving under appropriate temperature and pressure conditions. Customary care should be exercised so that no incompatible conditions exist between the active components and the diluent preservative or flavoring agent, or in the conditions employed in preparation of the compositions.

Typical formulations of the type listed above, which may be used for the administration of these compounds are:

EXAMPLE 3

Hard gelatin capsules can be prepared by filling standard two-piece hard gelatin capsules with the following mixture using conventional encapsulating equipment:

| | |
|---|---|
| Levorotatory enantiomer of molindone | 10 mg. |
| Lactose | 100 mg. |
| Talc | 10 mg. |
| Magnesium Stearate | 4 mg. |

EXAMPLE 4

A mixture or active drug in soy bean oil is prepared and injected by means of a positive displacement pump in gelatin to form soft gelatin capsules. A soft gelatin capsule will contain 10 mg. of active ingredient. The capsules are washed in petroleum ether and dried.

EXAMPLE 5

Tablets can be prepared by conventional procedures so that each tablet will contain:

| | |
|---|---|
| Levorotatory enantiomer of molindone | 10 mg. |
| Spray-Dried Lactose | 125 mg. |

| -continued | |
|---|---|
| Microcrystalline Cellulose | 30 mg. |
| Polyvinylpyrolidone | 3 mg. |
| Magnesium Stearate | 4 mg. |

EXAMPLE 6

An aqueous solution for oral administration is prepared so that each 5 ml. contains

| | |
|---|---|
| Levorotatory enantiomer of molindone | 5 mg. |
| Carboxy Methyl Cellulose | 5 % w/v |
| Syrup | 35 % v/v |
| Glycerin | 10 % v/v |
| Sorbitol | 10 % v/v |
| Sodium Metabisulfite | 5 mg. |
| Propyl Paraben | 1 mg. |
| Methyl Paraben | 5 mg. |
| Butterscotch flavor | 0.1 % v/v |
| Disodium Ethylenediaminetetraacetic Acid | 0.5 mg. |
| Water Q.S. | 5 cc. |

EXAMPLE 7

Parenteral composition suitable for intramuscular and intravenous administration is prepared so that each ml. contains:

| | |
|---|---|
| Levorotatory enantiomer of molindone | 10 mg. |
| Sodium chloride - add enough quantity to make isotonic solution | |
| Benzyl Alcohol | 1.5 % |
| Water for Inj. Q.S. | 1 ml. |

EXAMPLE 8

A suitable number of suppositories is prepared so that each suppository contains:

| | |
|---|---|
| Levorotatory enantiomer of molindone | 10 mg. |
| Polyethylene Glycol 4000 | 1.5 gm |
| Polyethylene Glycol 1000 | 1.5 gm. |

Melt the Polyethylene Glycol 4000 and Polyethylene Glycol 1000. Add the active ingredient while mixing. Pour into suppository molds and cool.

What is claimed is:

1. The levorotatory enantiomer of 3-ethyl-6,7-dihydro-2-methyl-5(morpholinomethyl)indol-4 (5H)-one or a pharmaceutically acceptable acid addition salt thereof in the absence of any substantial amount of the dextrorotatory enantiomer.

2. A antidepressant composition comprising a pharmaceutically suitable carrier and an effective amount of the levorotatory enantiomer of claim 1 or a pharmaceutically acceptable acid addition salt thereof.

3. A method of producing an antidepressant effect in warm-blooded animals comprising administering to said warm-blooded animals an effective antidepressant amount of the levorotatory enantiomer of claim 1 or a pharmaceutically acceptable acid addition salt thereof.

* * * * *